United States Patent [19]

Lin

[11] Patent Number: 4,736,628

[45] Date of Patent: Apr. 12, 1988

[54] TESTING DEVICE FOR CAR BATTERY AND RADIATOR

[76] Inventor: Victoria S. Lin, 2F, No. 114, Sec. 2, Fu-Shin South Road, Taipei, Taiwan

[21] Appl. No.: 54,525

[22] Filed: May 27, 1987

[51] Int. Cl.⁴ ............................................. G01N 9/10
[52] U.S. Cl. .................................................... 73/440
[58] Field of Search .......................... 73/440, 445, 444

[56] References Cited

U.S. PATENT DOCUMENTS 4,649,747  3/1987  Barber et al. ......................... 73/440
4,702,109  10/1987  Viola ..................................... 73/440

Primary Examiner—Stewart J. Levy
Assistant Examiner—Robert P. Bell
Attorney, Agent, or Firm—Morton J. Rosenberg

[57] ABSTRACT

A box-like housing which is enclosed to form a chamber. The chamber is partitioned by wall-like structure and further forms a plurality of channels in which a plurality of balls having various densities are contained within the channels. Measuring fluid flows through one end of tubular element mounted on the top of housing and into the channel, and the number of floating balls indicates the specific gravity of fluid and the freezing and boiling point of the fluid.

1 Claim, 6 Drawing Sheets

FIG_1

FIG_3

TESTING DEVICE FOR CAR BATTERY AND RADIATOR

BACKGROUND OF THE INVENTION

Conventional hydrometers for battery fluid comprise a cylindrical rod having fixed specific gravity calibrations enclosed within an enclosure with suction means. When such a device is to be used to measure the specific gravity of battery fluid, a sample of battery fluid is drawn from the battery and the device is placed vertically to read the calibration on the cylindrical rod, however, the readings from the calibration are usually inaccurate. Besides, if the temperature of the measuring fluid is either too high or too low, it is rather difficult to hold the hydrometer vertically with hands in order to read the calibrations. Therefore, conventional hydrometers possess drawbacks which are to be overcome.

SUMMARY OF THE INVENTION

It is therefore an objective of the present invention to provide a testing device for car batteries and radiators wherein the device functions as a hydrometer and can also be used to measure the freezing point and boiling point of the fluid in the radiator.

It is another objective of the present invention to provide a testing device for car batteries and radiators which is easily operated by connecting at the passageway of battery fluid and water supply to the radiator.

It is a further objective of the invention to provide a testing device for car batteries and radiators which is strong and durable yet pleasing in appearance and economical to manufacture.

It is another objective of the present invention to provide a testing device for car batteries and radiators which can be used in either a very high temperature or very low temperature.

It is a further objective of the present invention to provide a testing device for car batteries and radiators which can be connected firmly during the testing operation.

Other objectives, together with the foregoing, are attained in the embodiment of the invention described in the accompanying description and illustrated in the accompanying drawings.

DETAILED DESCRIPTION OF THE INVENTION

Figure 1:
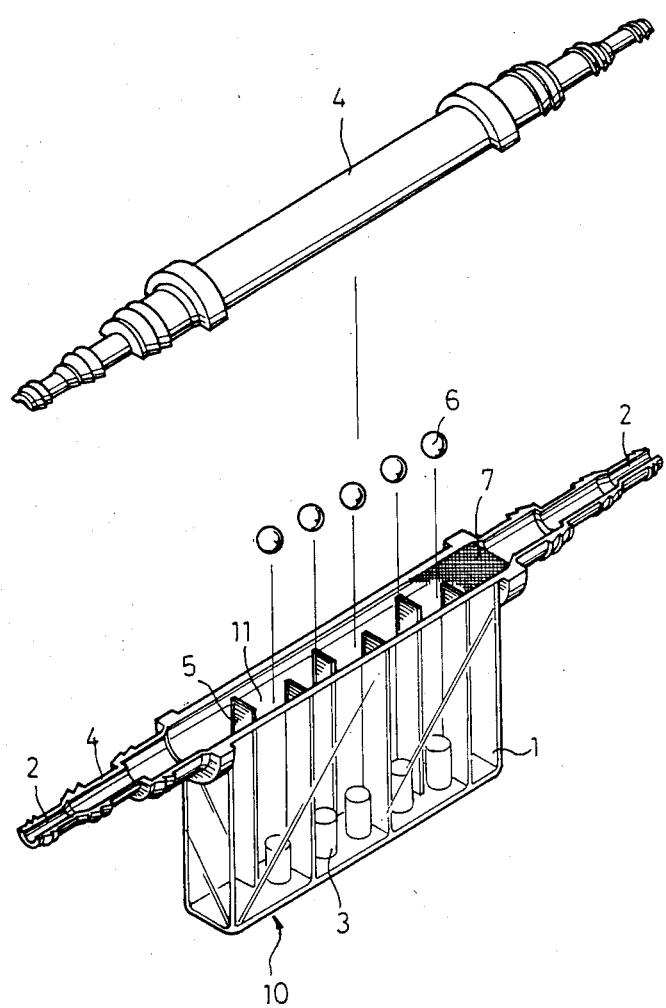
FIG. 1 is constitutional pictoral drawing of the testing device in accordance with the present invention.
Figure 2:
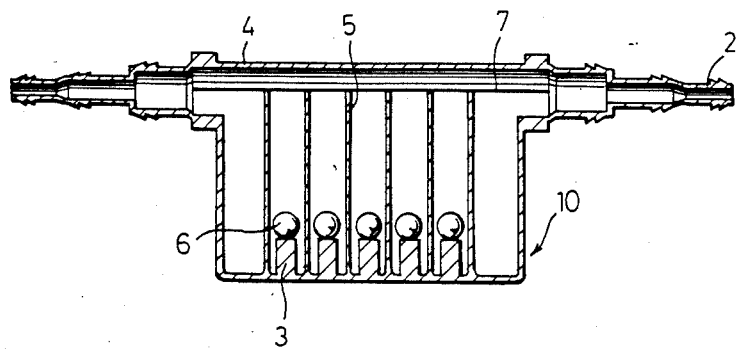
FIG. 2 is a cross-sectional view of the testing device.
Figure 3:
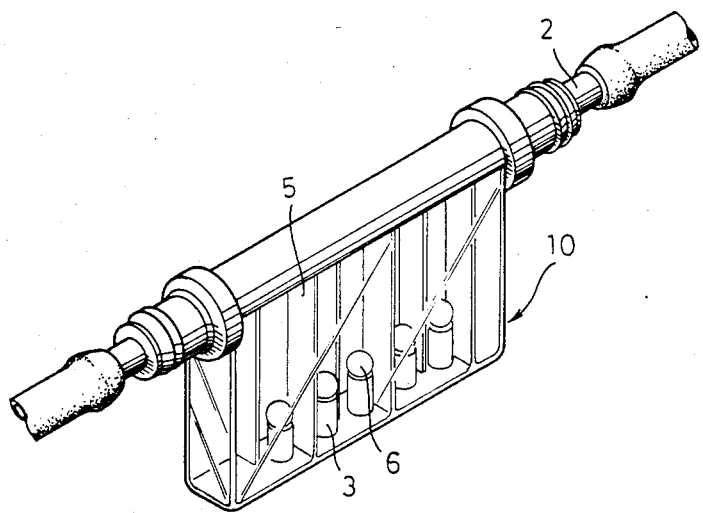
FIG. 3 is a perspective view of the testing device showing the connection at a passageway of fluid supply or discharge.

As shown in FIG. 1 to 3, a testing device 10 of substantially box-like structure, is generally transparent with housing 1 wherein the housing 1 is vertically partitioned and carefully spaced and mounted with a plurality of partition walls 5 and forms a plurality of channels 11. Generally, the dimensions of said partition walls 5 are adapted to fit within the interior of housing 1 and are alternatively arranged adjacent to the front face and rear face of the housing 1. As a result, the interior of the housing 1 is not individually isolated by said partition wall 5 but in communication among said channels 11. At the base of said housing 1 and in alignment with each channel 11, short cylindrical structures 3 are mounted, such that a plurality of balls 6 of various densities can be supported on said structure 3. It has a tubular element 4 with a filter sheet 7 horizontally mounted on the top of said partition wall 1 wherein said filter sheet 7 blocks any impurities of the fluid that pass therethrough. The end portion 2 of said tubular element 4 forms the inlet and outlet for the flowing of battery fluid or water of the radiator.

Generally, the above-mentioned balls 6 are denoted with colors for the different density reference. The floatation of these colored balls 6 depends on the specific gravity of the measuring fluid. That is to say, the number of floating balls 6 that float within the housing 1 indicates the specific gravity of the measuring fluids.

The end portions 2 of the tubular element 4 are designed with variable diameters and segmented at selected regions such that the device 10 is adaptable to any size of base from the battery.

A sticker printed with calibrations of temperature and specific gravity with respect to the number of floating balls may be stuck on the surface of said housing 1, or said calibrations may be silk-screened on the surface of said housing 1.

In the preferred embodiment of the present invention, the testing device is provided at a selected position on a passageway of a recycle system of a radiator or battery. The passageway, usually a rubber hose, is cut into two ends and the end portions of the tubular element 4 are individually connected to the ends of the hose. Therefore, the recyling of the measuring fluid through the device 10 effects the floatation of the colored balls 6.

Figure 4:
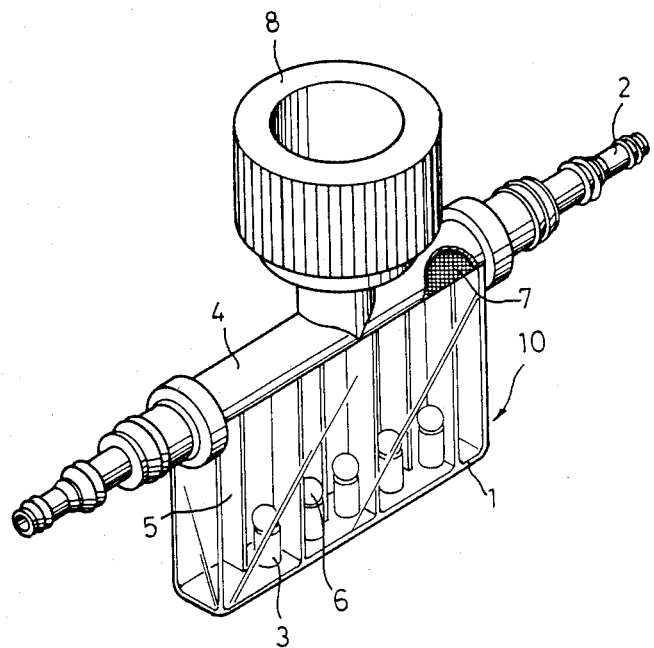
FIG. 4 and FIG. 5 are further embodiments of the testing device which can be mounted at a manifold at a passageway of fluid supply or discharge.

FIG. 4 illustrates a further embodiment of the testing device in accordance with the present invention. It can be seen that a manifold is adapted with a cap 8 having a testing device according to the present invention is mounted onto the top surface of said cap 8 as shown in the figure. The modification allows the testing device to be easily capped in for the determination of the specific gravity of the fluid, or fluid freezing point or boiling point.

Figure 5:
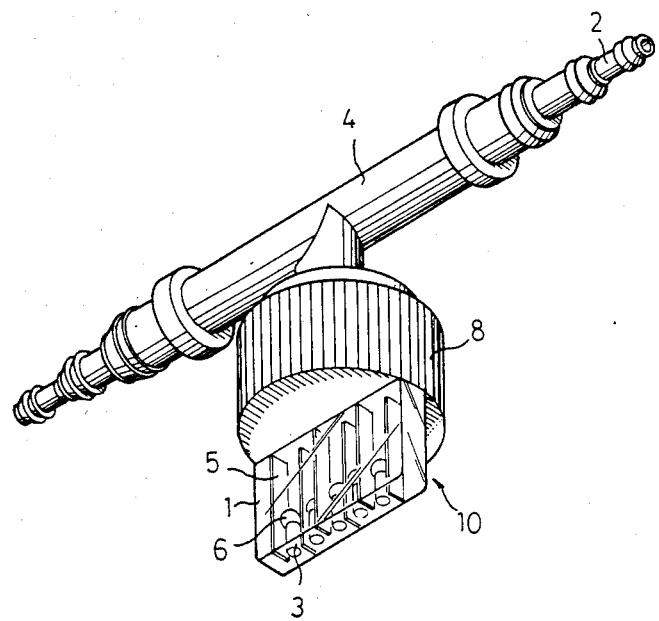

FIG. 5 shows another embodiment of the present invention in which an additional outlet is provided on a tubular element 4. The outlet is sealed with a cap 8 such that when anti-freeze agent or coolant is added to the radiator due to the abnormal condition of the fluid, the cap is unscrewed and allows the fluid to be discharged. As a result, the filling of the appropriate agent can be facilitated.

Figure 6:
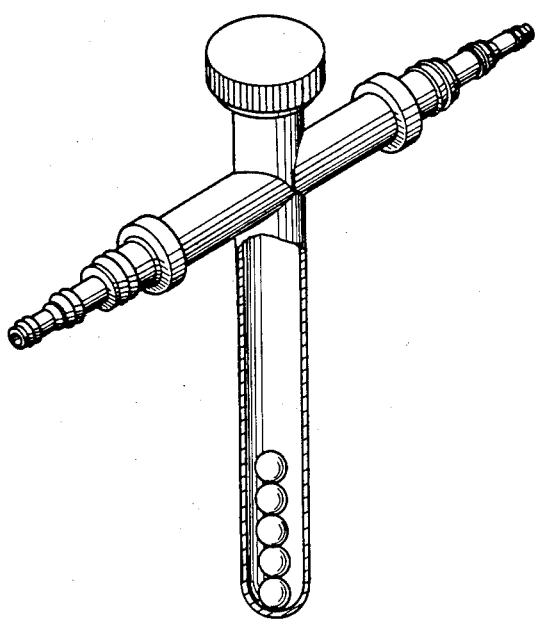
FIG. 6 is a perspective view of another embodiment of the testing device in accordance with the present invention.

FIG. 6 is another embodiment showing another form of testing device in accordance with the present invention.

In like manner other variations within the scope of the invention may occur to those skilled in the art. It is therefore desired that the scope of the invention be measured by the appended claims rather than by the purely illustrative embodiments shown and described herein.

I claim:

1. A testing device for car batteries and radiators adaptable to a selected region of a recycle system for measuring the specific gravity of fluid and freezing or boiling point of fluid, comprising:
(a) a transparent box-like housing, a tubular element having a plurality of end diameters being mounted on top of said housing for communicating with a stream of fluid;
(b) a plurality of partition walls vertically mounted to the interior base of said housing, said partition walls alternately being positioned adjacent to the front face and rear face of said housing;
(c) a plurality of channels formed by said partition walls within said housing, said channels being in communication with said tubular element;
(d) a plurality of balls with different densities, each of said balls being enclosed in one of said channels within said housing so that fluid flowing therethrough effects the floatation of said balls;
(e) a plurality of cylindrical structures, each of said cylindrical structures being vertically mounted on the respective interior bases of each of said channels for the retaining of said balls;
(f) two end portions attaching to the ends of said tubular element, said end portions being tapered outward ;
(g) a filter sheet horizontally mounted on the top of said partition walls and enclosed within said tubular element so as to filter fluid flowing therethrough.

* * * * *